(12) United States Patent
Wu

(10) Patent No.: US 9,291,802 B2
(45) Date of Patent: Mar. 22, 2016

(54) COMPACT LABEL FREE IMAGING SYSTEM

(75) Inventor: Qi Wu, Painted Post, NY (US)

(73) Assignee: Corning Incorporated, Corning, NY (US)

(*) Notice: Subject to any disclaimer, the term of this patent is extended or adjusted under 35 U.S.C. 154(b) by 725 days.

(21) Appl. No.: 13/371,693

(22) Filed: Feb. 13, 2012

(65) Prior Publication Data

US 2012/0274820 A1    Nov. 1, 2012

Related U.S. Application Data

(60) Provisional application No. 61/480,698, filed on Apr. 29, 2011.

(51) Int. Cl.
| | |
|---|---|
| *G02B 13/16* | (2006.01) |
| *G02B 13/22* | (2006.01) |
| *G01N 21/25* | (2006.01) |
| *G01N 21/552* | (2014.01) |
| *G01N 21/65* | (2006.01) |
| *H04N 5/225* | (2006.01) |
| *G01N 21/77* | (2006.01) |

(52) U.S. Cl.
CPC .............. *G02B 13/22* (2013.01); *G01N 21/253* (2013.01); *G01N 21/553* (2013.01); *G01N 21/658* (2013.01); *G01N 21/7743* (2013.01)

(58) Field of Classification Search
CPC ... G02B 13/22; G01N 21/253; G01N 21/553; G01N 21/658
USPC .................................................. 348/335, 340
See application file for complete search history.

(56) References Cited

U.S. PATENT DOCUMENTS

| | | | | |
|---|---|---|---|---|
| 7,057,720 | B2* | 6/2006 | Caracci et al. ................ | 356/300 |
| 7,175,980 | B2 | 2/2007 | Qiu et al. .......................... | 435/4 |
| 7,292,333 | B2* | 11/2007 | Fontaine .............. | G01N 21/253 356/300 |
| 7,336,354 | B2* | 2/2008 | Sun .......................... | G01J 3/02 356/318 |
| 7,599,055 | B2* | 10/2009 | Gollier et al. ................ | 356/246 |
| 8,213,017 | B2* | 7/2012 | Wiki .................... | G01N 21/253 356/445 |
| 8,384,905 | B2* | 2/2013 | Wu .......................... | G01J 3/10 356/218 |
| 2004/0130723 | A1 | 7/2004 | Yager et al. | |
| 2006/0223111 | A1* | 10/2006 | Chow et al. .................... | 435/7.1 |
| 2007/0114362 | A1* | 5/2007 | Feng et al. ................. | 250/208.1 |
| 2007/0141231 | A1* | 6/2007 | Qiu et al. ..................... | 427/2.11 |

(Continued)

FOREIGN PATENT DOCUMENTS

WO     2006/108183     10/2006

OTHER PUBLICATIONS

International Search Report and Written Opinion issued on Aug. 8, 2012 in corresponding PCT Application Serial No. PCT/US2012/033860, filed Apr. 17, 2012.

(Continued)

*Primary Examiner* — Ngoc-Yen Vu
(74) *Attorney, Agent, or Firm* — John L. Haack

(57) ABSTRACT

A compact microplate imaging system, including: a tunable light source; a lens ensemble to collimate the light source onto the microplate and to transmit light that is reflected from the microplate; a beam splitter to divert a portion of the reflected light; an imaging lens to collect diverted light and to produce an optical image of the at least one sensor of the microplate; and an image sensor for receiving the optical image of the at least one sensor of the microplate. A method for interrogating a sensor using the compact microplate imaging system, as further defined herein, is also disclosed.

18 Claims, 10 Drawing Sheets

(56) References Cited

U.S. PATENT DOCUMENTS

2008/0204760 A1    8/2008   Gollier et al.
2009/0251791 A1   10/2009   Seward
2012/0064519 A1*   3/2012   Fang ................. G01N 21/7743
                                                             435/6.1

OTHER PUBLICATIONS

Fang, et al., "Resonant Waveguide Grating Biosensor for Living Cell Sensing", Biophysical Journal, vol. 91, (2006), pp. 1925-1940.

* cited by examiner

COMPACT LABEL FREE IMAGING SYSTEM

This application claims the benefit of priority under 35 U.S.C. §119 of U.S. Provisional Application Ser. No. 61/480,698, filed on Apr. 29, 2011, the content of which is relied upon and incorporated herein by reference in its entirety.

BACKGROUND

The disclosure generally relates to an compact apparatus and method for imaging a sensor.

SUMMARY

The disclosure provides a compact apparatus and method for imaging a sensor, for example, as used in a microplate optical reader for label-independent detection.

BRIEF DESCRIPTION OF THE DRAWING(S)

In embodiments of the disclosure:

FIG. 1 is a schematic of an exemplary compact label free imaging system.

FIG. 2 graphically shows the resonant wavelength of a resonant waveguide (RWG) sensor as a function of the interrogation angle.

Figure 7A:
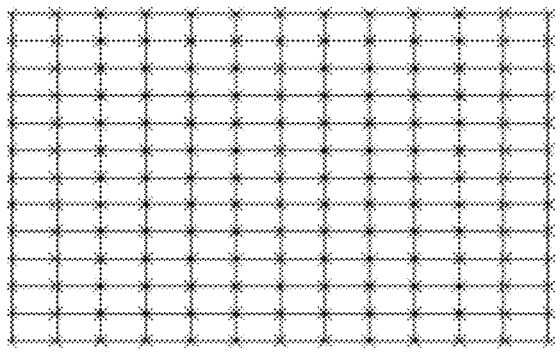
Figure 7B:
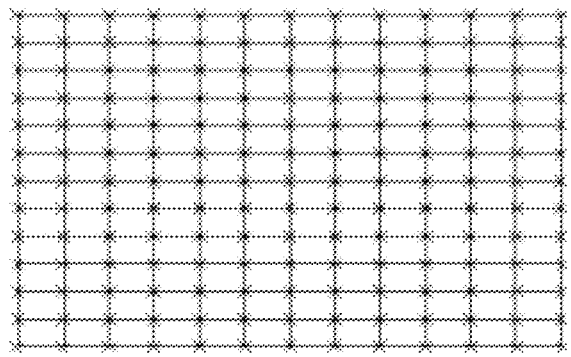

FIGS. 7A and 7B, respectively, show a grid distortion of the spherical optics imaging system that has been minimized to 0.43% (7A); and a grid distortion of the aspheric optics imaging system that has been minimized to 0.27% (7B).

Figure 8:
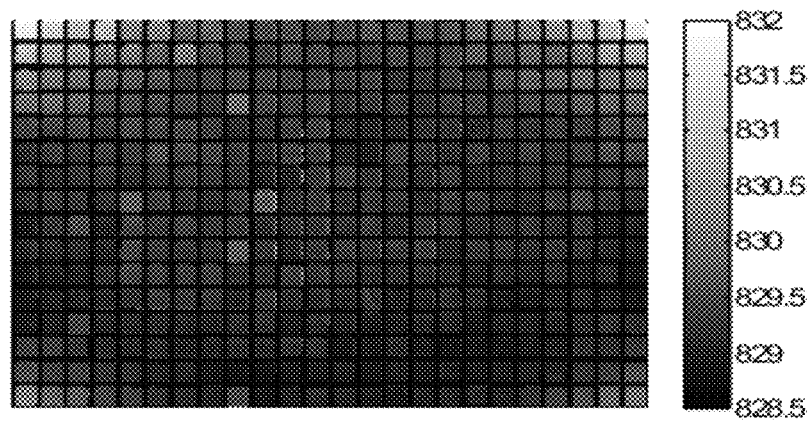

FIG. 8 shows a resonant wavelength gray-scale version of a color image of a sensor microplate measured using the edge effects system having a dual bi-convex objective lens.

Figure 9:
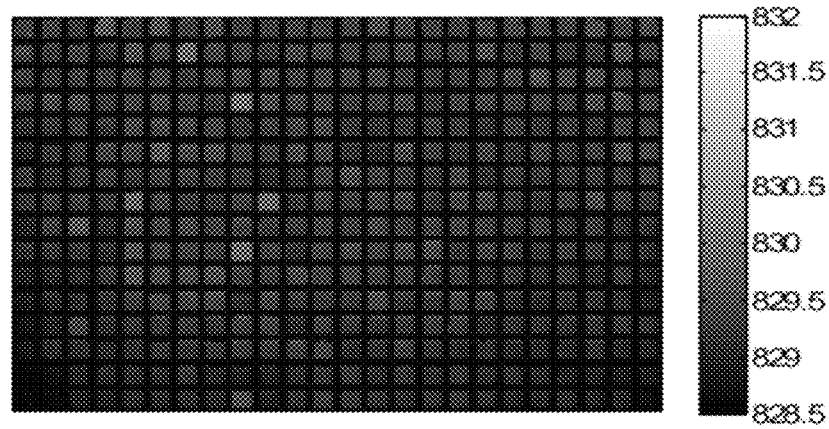

FIG. 9 shows a resonant wavelength gray-scale version of a color image of a sensor microplate measured using the system having aspheric objective lens.

Figure 10:
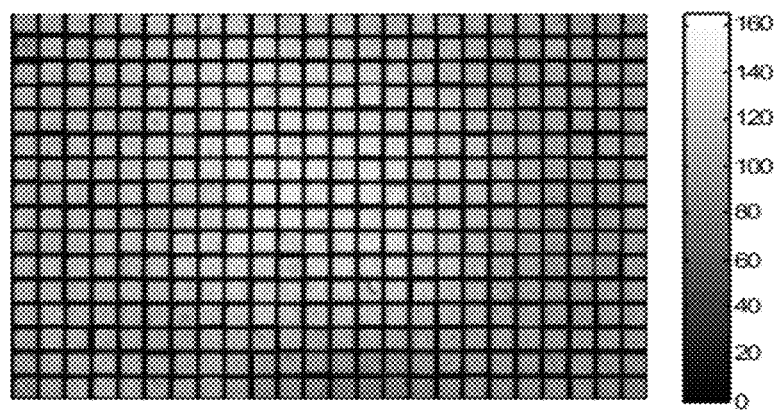

FIG. 10 shows a resonant optical power gray-scale version of a color image of a sensor microplate measured using the system having a dual bio-convex objective lens.

Figure 11:
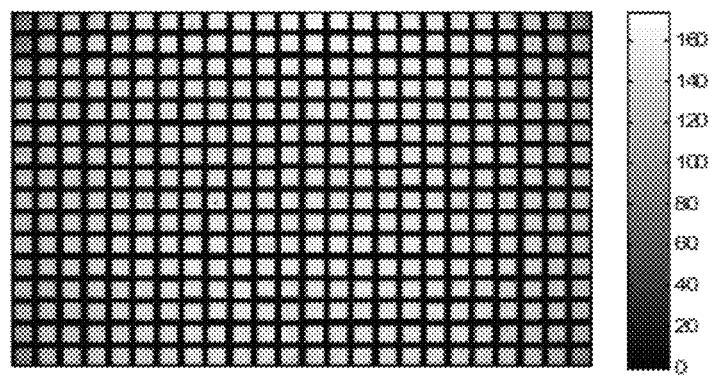

FIG. 11 shows a resonant optical power gray-scale version of a color image of a sensor microplate measured using the system having a aspheric objective lens.

Figure 12:
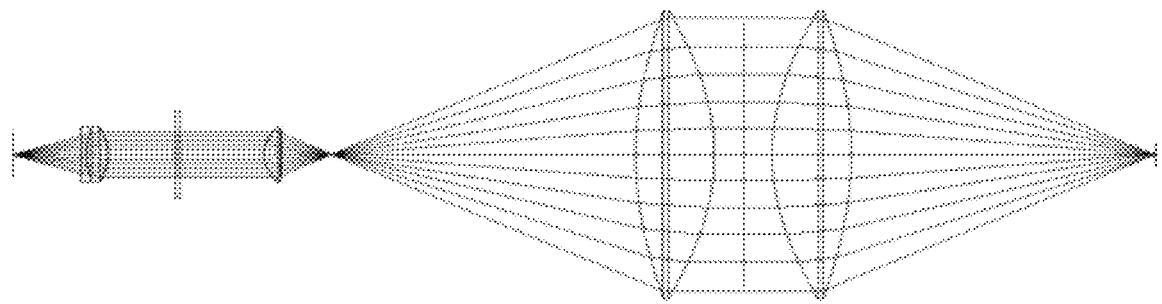

FIG. 12 shows an unfolded optical layout based on a single element aspheric objective to correct spherical aberration.

Figure 13A:
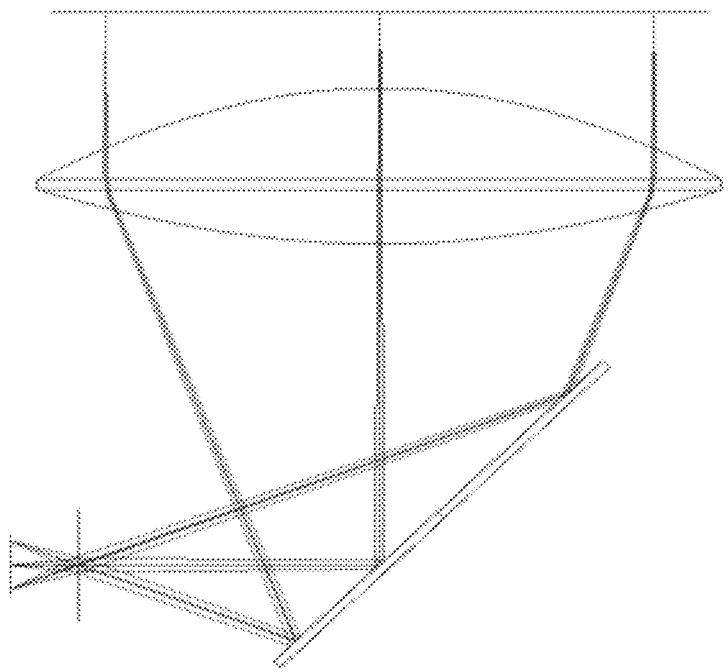

FIG. 13a shows a 12 mm focal length used for achieving further reduced instrument height.

Figure 13B:
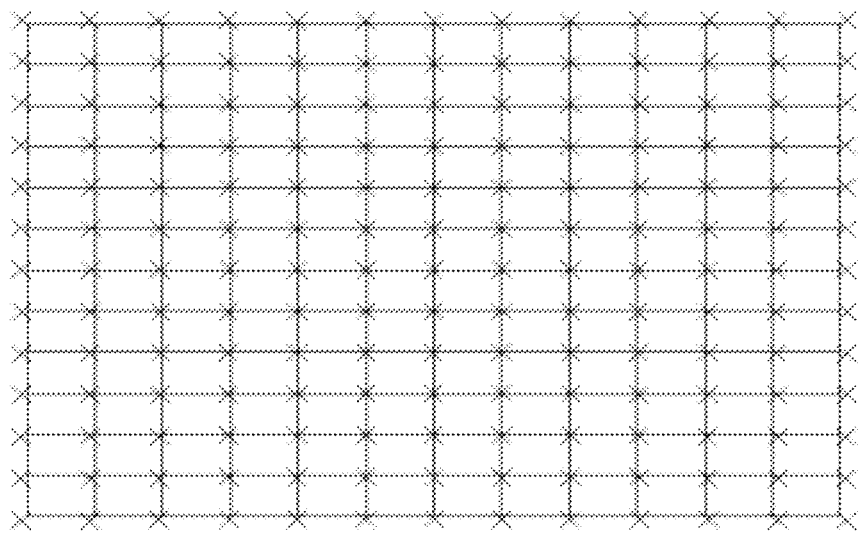

FIG. 13b shows image distortion designed to be 1.5% to compensate for the −1.5% distortion of the CCD lens.

Figure 14:
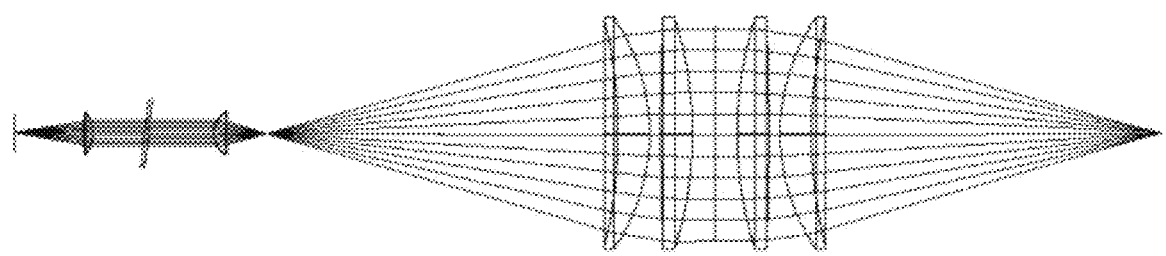

FIG. 14 shows an unfolded optical layout based on a superior dual element spherical objective lens design for full plate imaging.

Figure 15:
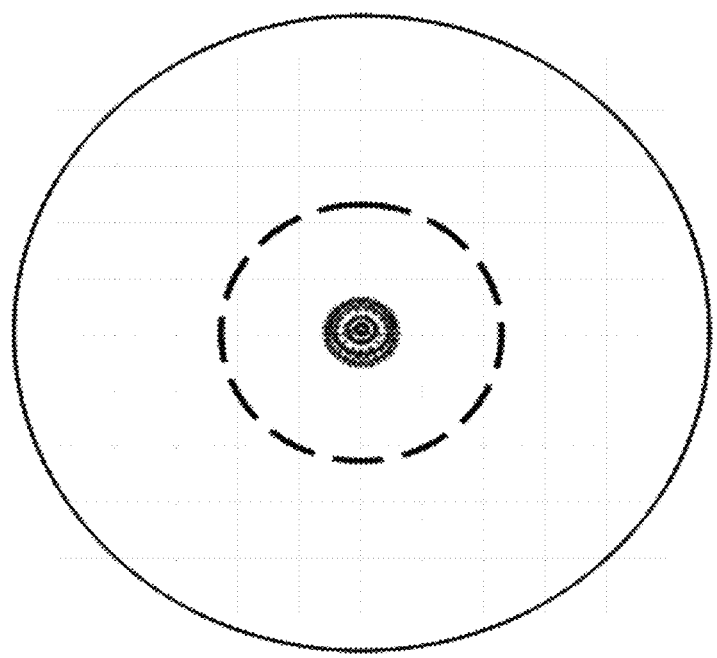

FIG. 15 shows spot diagrams at the aperture stop plane of the imaging lens as compared to the iris size of a 16 mm F1.4 lens (solid line) and a 6 mm F1.4 lens (dashed line).

Figure 16:
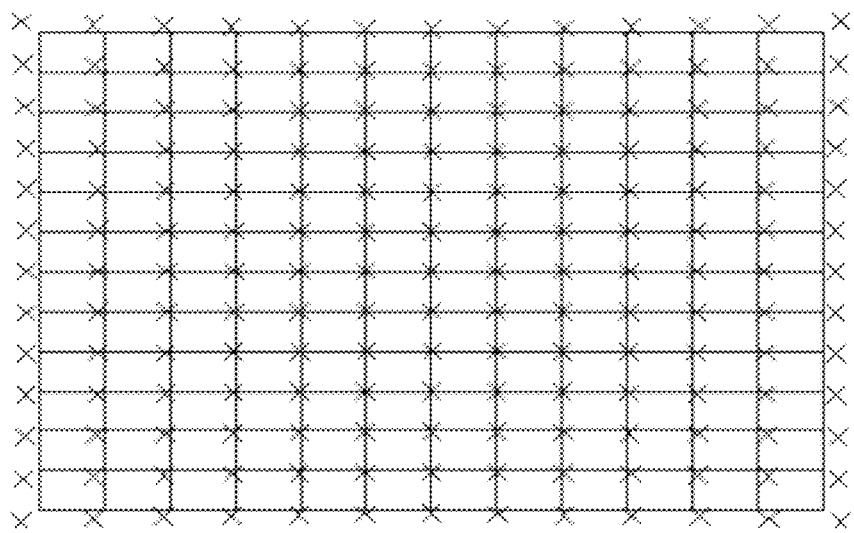

FIG. 16 shows the grid distortion of the spherical optics imaging system is about 4.5%.

Figure 17:
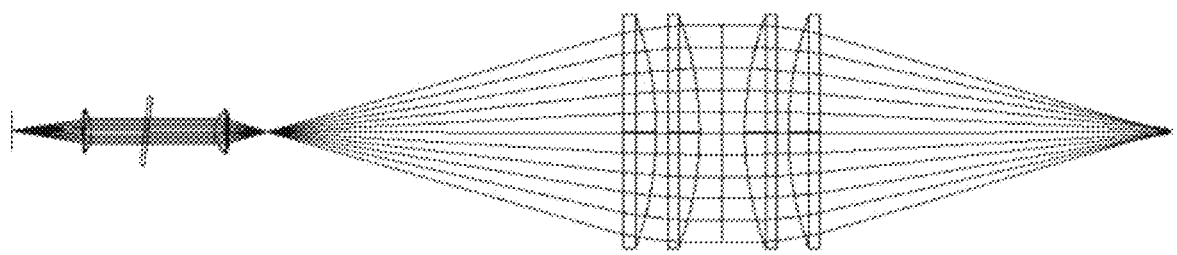

FIG. 17 shows an unfolded optical layout based on a dual plano-convex spherical objective lens design for full plate imaging.

Figure 18:
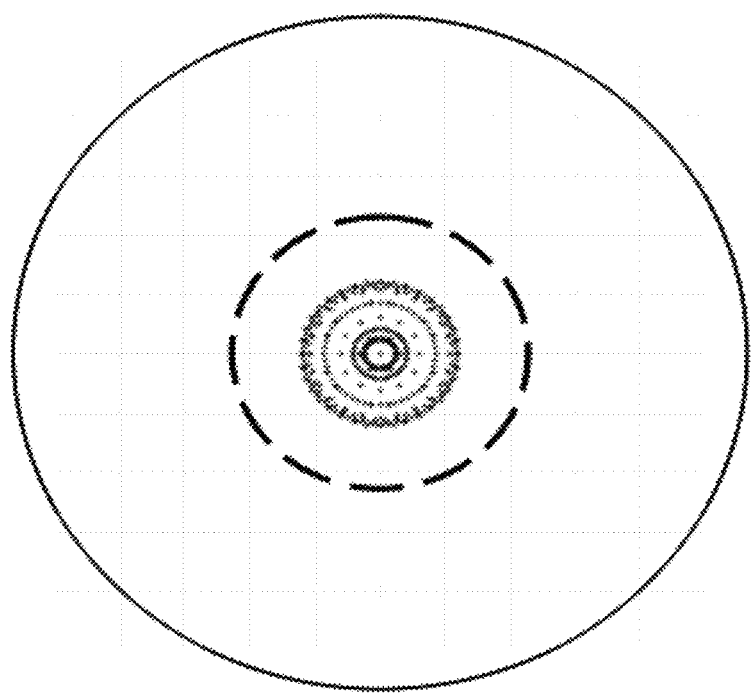

FIG. 18 shows spot diagrams at the aperture stop plane of the imaging lens as compared to the iris size of a 16 mm F1.4 lens (solid line) and a 6 mm F1.4 lens (dashed line).

DETAILED DESCRIPTION

Various embodiments of the disclosure are described in detail with reference to the drawings. Reference to various embodiments does not limit the scope of the invention, which is limited only by the scope of the claims. Additionally, any examples set forth in this specification are not limiting and merely set forth some of the many possible embodiments for the claimed invention. Any aspect, feature, or embodiment of the disclosure can be used in any combination or permutation with any one or more other aspect, feature, or embodiment recited in the appended claims.

DEFINITIONS

"Biosensor," "sensor," or like term refers to an article, that in combination with appropriate apparatus, can detect a desired analyte or condition. A biosensor combines a biological component with a physicochemical detector component. A biosensor can typically consist of three parts: a biological component or element (such as tissue, microorganism, pathogen, cells, cell component, a receptor, and like entities, or combinations thereof), a detector element (operating in a physicochemical way such as optical, piezoelectric, electrochemical, thermometric, magnetic, or like manner), and a transducer associated with both components. In embodiments, the biosensor can convert a molecular recognition, molecular interaction, molecular stimulation, or like event occurring in a surface bound cell component or cell, such as a protein or receptor, into a detectable and quantifiable signal. A biosensor as used herein can include liquid handling systems which are static, dynamic, or a combination thereof. In embodiments of the disclosure, one or more biosensor can be incorporated into a micro-article. Biosensors are useful tools and some exemplary uses and configurations are disclosed, for example, in PCT Application No. PCT/US2006/013539 (Pub. No. WO 2006/108183), published Dec. 10, 2006, to Fang, Y., et al., entitled "Label-Free Biosensors and Cells," and U.S. Pat. No. 7,175,980. Biosensor-based cell assays having penetration depths, detection zones, or sensing volumes have been described, see for example, Fang, Y., et al. "Resonant waveguide grating biosensor for living cell sensing," *Biophys. J.*, 91, 1925-1940 (2006). Microfluidic articles are also useful tools and some exemplary uses, configurations, and methods of manufacture are disclosed, for example, in U.S. Pat. Nos. 6,677,131, and 7,007,709. U.S. Patent Publication 2007/0141231 and U.S. Pat. No. 7,175,980, disclose a microplate assembly and method. These documents are hereby incorporated by reference in their entirety.

The apparatus and methods of the disclosure are particularly well suited for biosensors based on label-independent detection (LID), such as for example an Epic® system or those based on surface plasmon resonance (SPR). The articles, and methods of the disclosure are also compatible with an alternative LID sensor, such as Dual Polarized Intereferometry (DPI). In embodiments, the biosensor system can comprise, for example, a swept wavelength optical interrogation imaging system for a resonant waveguide grating biosensor, an angular interrogation system for a resonant waveguide grating biosensor, a spatially scanned wavelength interrogation system, surface plasmon resonance imaging, and like systems and applications, or a combination thereof.

Commonly owned and assigned copending U.S. patent application Ser. Nos. 13/021,945 and 12/939,606 disclose systems and methods for optically reading microplates. These documents and their corresponding provisional applications are hereby incorporated by reference in their entirety.

"About" modifying, for example, the quantity, dimension, process temperature, process time, and like values, and ranges thereof, employed in describing the embodiments of the disclosure, refers to variation in the numerical quantity that can occur, for example: through typical measuring and handling procedures used; through inadvertent error in these procedures; through differences in the manufacture, source, or quality of components and like considerations. The term "about" also encompasses amounts that differ due to aging of or environmental effects on components. The claims appended hereto include equivalents of these "about" quantities.

"Optional," "optionally," or like terms refer to the subsequently described event or circumstance can or cannot occur, and that the description includes instances where the event or circumstance occurs and instances where it does not. For example, the phrase "optional component" or like phrase means that the component can or can not be present and that the disclosure includes both embodiments including and excluding the component.

"Consisting essentially of" in embodiments refers, for example, to optical readers and associated components, to an assay, to method of using the assay to screen compounds, and to articles, devices, or any apparatus of the disclosure, and can include the components or steps listed in the claim, plus other components or steps that do not materially affect the basic and novel properties of the articles, apparatus, or methods of making and use of the disclosure, such as particular components, a particular light source or wavelength, a particular surface modifier or condition, or like structure, material, or process variable selected. Items that may materially affect the basic properties of the components or steps of the disclosure or that may impart undesirable characteristics to aspects of the disclosure include, for example, having a disfavored orientation of the radiation source or the image recorder.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, and "rt" for room temperature, "nm" for nanometers, and like abbreviations).

Specific and preferred values disclosed for components, times, operations, and like aspects, and ranges thereof, are for illustration only; they do not exclude other defined values or other values within defined ranges. The article, apparatus, and methods of the disclosure include those having any value or any combination of the values, specific values, more specific values, and preferred values described herein.

The Corning, Inc., Epic® system is a high throughput label free detection technology platform for studying bio-molecular interactions and live cells. A commercially available Epic® instrument can detect the average response of each biosensor in a microplate. Label free imaging methods continue to evolve and can now provide spatially resolved high content label free responses within each sensor (see for example, commonly owned and assigned U.S. Pat. No. 7,599,055, to Gollier et al., entitled "Swept wavelength imaging optical interrogation system and method for using same"). This document is hereby incorporated by reference in its entirety.

In embodiments, the disclosure provides a compact and low cost apparatus and a method for optical reader imaging for biochemical, live-cell, and like label-independent-detection (LID) assays.

Swept wavelength imaging system for interrogating a resonant waveguide grating (RWG) based Epic® biosensor has been described and demonstrated, see for example, commonly owned and assigned U.S. Pat. No. 7,599,055. The optical system described in U.S. Pat. No. 7,599,055, was designed to interrogate an entire SBS format microplate. The technology recently evolved from using a narrow band tunable laser to a tunable light source with optimum temporal and spatial coherence (see commonly owned and assigned copending U.S. Ser. No. 12/939,606, entitled "Tunable light source for label independent optical reader," first filed Nov. 10, 2009). The tunable light source is much lower in cost compared to tunable lasers and commercially available tunable filters. More importantly, the tunable light source eliminated optical speckles and simplified data processing. Initial demonstration of the tunable light source was based on an imaging system with a field of view covering 4×3 wells of a microplate and using primarily optics with one (1) inch diameter.

Scaling-up the functionality of the instrument described in copending U.S. Ser. No. 12/939,606, follows similar strategies described in U.S. Pat. No. 7,599,055. In one approach, the light source was optically expanded to illuminate the desired plate area, and a telecentric lens imaged the illuminated area into an image sensor. However, having separate illumination and imaging optics, the resulting instrument has a relatively large footprint (e.g., about 24×12 or about 288 square inches).

Although fluorescence imaging plate readers (FLIPR) (see J. Wu Jiang, et al., "Fast and wide-field reflective optic system for imaging microplate readers," Proc. SPIE, v 5328, n 1, p 87-96, (2004)), are widely used in the study of ion channel cell assays, and there are also reports on measuring reflectometric interference spectroscopy (RiFS) sensors in microplate format (see O. Birkert, et al., "Label-free parallel screening of combinatorial triazine libraries using reflectometric interference spectroscopy," Analytical Chemistry, v 74, n 4, p 834-840, (2002)), these optical systems are designed either for efficient fluorescence collection or off-normal angle imaging. Optical design criteria for imaging full plate RWG sensors are significantly different.

In embodiments, the present disclosure provides a more compact architecture than previous systems that can include, for example, sharing a single common wide-field telecentric (WFT) objective lens that can be used for both illumination and imaging. Maximizing the effectiveness of the WFT objective lens is a significant aspect of the system performance. In embodiments, the present disclosure provides a design and implementation of the improved compact label-free imaging system.

In embodiments, the disclosure provides design and enhancement of a compact, cost effective, and scalable optical system for label-free imaging. A WFT objective lens or lens group can be shared between the illumination beam expansion path and the imaging path. A dual bi-convex optical design was demonstrated in a compact full plate imaging system. The optical performance can be enhanced, for example, by replacing one of the bi-convex lenses with an aspheric lens. In embodiments, a single element bi-aspheric objective lens design is provided which enables further reduction of the instrument size. In embodiments, another design provides performance enhanced spherical optics for low spherical aberration at the expense of image distortion.

The disclosed optical design has a much smaller footprint (e.g., about 10×4 or about 40 square inches compared to the about 24×12 or about 288 square inches) and much smaller overall dimensions (e.g., about 10×4×11 or about 440 cubic inches, and about 10×4×8 or about 320 cubic inches compared to about 24×12×18 or about 5184 cubic inches) than a previously demonstrated system, such as having from about 80 to about 95 percent smaller footprint and from about 90 to about 95 percent less volume.

An advantage of the disclosed WFT objective lens is that it is readily manufacturable and highly cost effective. The system is particularly effective at providing low image distortion and low spherical aberration. The aspheric design embodiment eliminates wavelength variation caused by spherical aberration, and enables low angle sensitivity across the plate. Using a single element bi-aspheric lens, the instrument height can be reduced to about 8 inches or less.

The radiation source can be, for example, a light emitting diode (LED), and like low- or non-coherent light sources. Other radiation sources can be selected if desired and properly adapted to the disclosed apparatus and method. The radiation source can alternatively be or additionally include, for example, a fluorescent source capable of providing a fluorescent incident beam or fluorescence inducing incident beam.

In embodiments, the disclosure provides a compact microplate imaging system, including:

a tunable light source having a spectral width substantially similar to the resonance width of at least one sensor of the microplate;

a lens ensemble to collimate the light source onto a user provided microplate and to transmit light that is reflected from the microplate;

a beam splitter to divert a portion of the reflected light;

an imaging lens to collect diverted light and to produce an optical image of the at least one sensor of the microplate; and an image sensor to receive the optical image of the at least one microplate sensor.

In embodiments, the disclosure provides a full-plate or microplate swept-wavelength imaging system, comprising:

a tunable light source having a spectral width substantially similar to the resonance width of at least one sensor of a full-plate, for example, from 0.3 time to 3 times the width of the resonance;

a lens ensemble for collimating the tunable light source on the full-plate and for transmitting any reflected light from the full-plate;

a beam splitter for diverting a portion of the transmitted light;

an imaging lens for collecting diverted light and producing an optical image of the at least one sensor of the full-plate; and an image sensor for receiving the optical image of the at least one sensor of the full-plate.

The lens ensemble can be, for example, a single focusing lens, such as for aspheric applications. Alternatively or additionally, the lens ensemble can be, for example, a lens group, such as for spherical applications. The lens group of the lens ensemble can be, for example, a focusing lens and an objective lens, such as focusing lens 340 and objective lens 110 (i.e., 120 and 130) shown in FIG. 1.

The lens ensemble can be selected to uniformly illuminate at least one microplate sensor, and preferably all the microplate sensors, of the full-plate or microplate at a normal incidence angle across the entire field to an accuracy of such as about 10 mrad, and more preferably 2 mrad, for example, from about 0.1 to 10 mrad, from about 0.1 to 5 mrad, from about 0.5 to 2 mrad, and which accuracy can depend upon the microplate flatness characteristics for the lower end of the mrad accuracy values.

The co-action of the focusing lens and the objective lens can be, for example, a beam expander.

In embodiments, the objective lens can be, for example, a lens group comprising two spherical lenses, see for example, working Examples 1 and 4 that mention plano-convex lenses.

In embodiments, the objective lens can be, for example, a single aspheric surface. In embodiments, the objective lens can be, for example, at least two aspheric surfaces.

In embodiments, the tunable light source can be, for example, a substantially collimated LED and tunable optical filter. The radiation source can be, for example, a light emitting diode (LED), and like low- or non-coherent light sources. Other radiation sources can be selected if desired and properly adapted to the disclosed apparatus and method. The radiation source can alternatively be or additionally include, for example, a fluorescent source capable of providing a fluorescent incident beam or fluorescence inducing incident beam.

In embodiments, the reflected beam from the at least one sensor of a microplate can pass through the same beam splitter, the imaging lens, and at least an objective lens of the lens ensemble, prior to forming an image on the image sensor.

In embodiments, the image sensor can be, for example, a CCD, a CMOS, and like image sensor devices, or a combination thereof.

Figure 6:
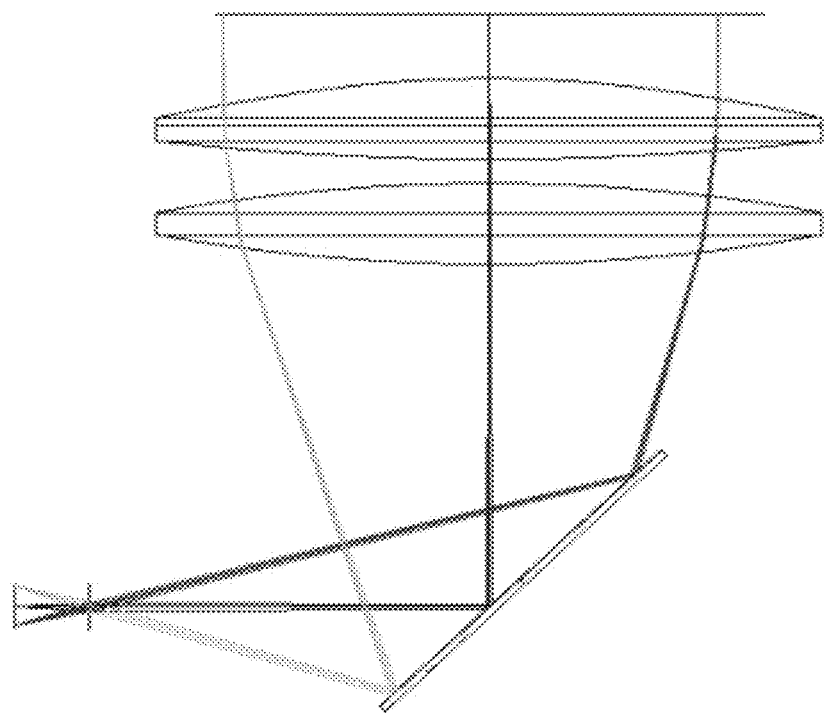
FIG. 6 shows a simulated imaging system assuming a perfect CCD imaging lens.

In embodiments, the optical stop of the imaging lens can be, for example, positioned at the focal point of the objective lens, see, for example, the aperture location shown in FIG. 6.

In embodiments, the single focusing lens can be an aspheric lens and can provide uniform illumination on a microplate. The aspheric lens preferably has low spherical aberration.

In embodiments, the distortion of the objective lens can compensate for the distortion from the imaging lens, including, for example, negative distortion, positive distortion, or combinations thereof.

In embodiments, the system is capable of simultaneously imaging fractional portions of a single microplate, a single full-plate, or a multiplicity of microplates. In embodiments, "a microplate" can be, for example, a multiplicity of microplates, such as from 2 to 20 or more plates. In embodiments, "a microplate" can be, for example, a fractional portion of a microplate, such as from ½, ⅓, ¼, ⅕, ⅙, and like fractions, including intermediate values and ranges.

In embodiments, the disclosure provides a method for interrogating a resonance waveguide (RWG) sensor of a microplate with any of the abovementioned systems or apparatus, comprising:

emitting an optical beam from the tunable source light source having a spectral width substantially similar to the resonance width of at least one sensor of the microplate;

converting the optical beam into one or more interrogation beams with the lens ensemble;

illuminating one or more sensors of the microplate with the one or more of the interrogation beams;

collecting the reflected light of the illuminated one or more plate sensors; and forming an image on the image sensor.

In embodiments, the disclosure provides an apparatus for label free imaging comprising:

an optical reader comprising:

a receptacle to receive a microplate having at least one optical sensor;

a tunable light source having a spectral width substantially similar to the resonance width of at least one sensor of the microplate;

a lens ensemble which collimates the tunable light source onto the microplate and transmits light reflected from the microplate;

a beam splitter which diverts a portion of the transmitted light;

an imaging lens which collects diverted light and produces an image beam; and an image sensor which receives and images the image beam.

In embodiments, the disclosure provides a method of reading an evanescent wave sensor in the abovementioned apparatus, comprising:

forming a microplate assembly by engaging the receptacle with a microplate having well, and at least one well having at least one optical sensor;

illuminating the microplate with the collimated tunable light source;

collecting the reflected light from the illuminated microplate; and forming an image of the reflected light on the image sensor.

The reader can have a spatial resolution, for example, of from about 0.5 to about 1,000 micrometers, from about 1 to about 1,000 micrometers, from about 1 to about 100 micrometers, from about 1 to about 10 micrometers, and from about 5 to about 10 micrometers, including any intermediate ranges and values.

The apparatus can further comprise, for example, a microplate, a well plate, a microscope slide, a chip format, or like analyte container, support member, or sample presentation article, and optionally including, for example, microfluidic flow facility. In embodiments, the apparatus can have at least one microplate, having at least one well, the well having the at least one optical sensor therein, and the sensor having a signal region and an optional reference region. The microplate can be an array of wells such as commercially available from Corning, Inc.

In embodiments, the disclosure provides a method of reading an evanescent wave sensor in the abovementioned apparatus having an engaged user-provided microplate having at least one sensor.

In embodiments, a received or provided microplate (workpiece) can have a base or substrate thickness, for example, of from about 10 micrometers to about 10,000 micrometers, about 50 micrometers to about 10,000 micrometers, and 100 micrometers to about 1,000 micrometers, including any intermediate values and ranges. A specific example of a microplate base thickness is, for example, of from about 0.1 millimeters to about 10 millimeters, such as 0.3 millimeters to about 1.0 millimeters. A thinner microplate base can, for example, reduce distortion and can improve image quality. A thin microplate base can be, for example, glass or like material having a thickness of about 0.7 mm to 1.0 mm and is representative of the thicknesses found in certain commercial products. Glass or like material having a thickness of less than about 0.4 mm is operatively a thin base plate material.

In embodiments, the incident beam can contact at least one optical sensor in, for example, at least one of: a single well, two or more wells, a plurality of wells, or preferably all wells of the received microplate.

The evanescent wave sensor can be, for example, a resonant waveguide biosensor, a surface plasmon resonance (SPR) sensor, and like sensors, or a combination of such sensors.

In embodiments, the sensor can include on its surface, for example, at least one of a live-cell, a bioentity, a chemical compound, a coating, and like entities, or a combination thereof.

The spatial resolution of the recorded image can be, for example, from about 0.5 to about 10 micrometers, including intermediate values and ranges, and the excellent spatial resolution can be sufficient to accomplish, for example, sub-cellular label-free imaging, and like imaging objectives.

In embodiments, the method can, for example, further comprise simultaneously or sequentially contacting the optical sensor with a fluorescence inducing incident beam and recording the received fluorescent image with a suitable recorder. That is, to accomplish, for example, cellular or sub-cellular fluorescence imaging (see, for example, commonly owned and assigned copending application U.S. Ser. No. 12/151,175, entitled "SYSTEM AND METHOD FOR DUAL-DETECTION OF A CELLULAR RESPONSE").

Although the sensor can be interrogated using swept wavelength imaging technique, a simpler intensity imaging technique which is commonly used in SPR imaging can be employed because of the wide resonance width. This method can be facilitated by the use of a low coherence light source, which removes the parasitic interference fringes (see for example commonly owned and assigned copending copending U.S. Ser. No. 61/259,802)

In embodiments, the disclosed imaging technique can be applied to compact Epic® configurations and applications by, for example, redesigning the field of view to cover 4×3 well-plate configurations, or like configurations. In embodiments, the disclosed system provides high spatial resolution and at reduced cost because the disclosed system can avoid a precision swept wavelength mechanism. The system's overall simplicity provides an optical reader having lower overall cost. However, in this operating mode the readout can be more sensitive to defects on the sensor surface.

Figure 1:
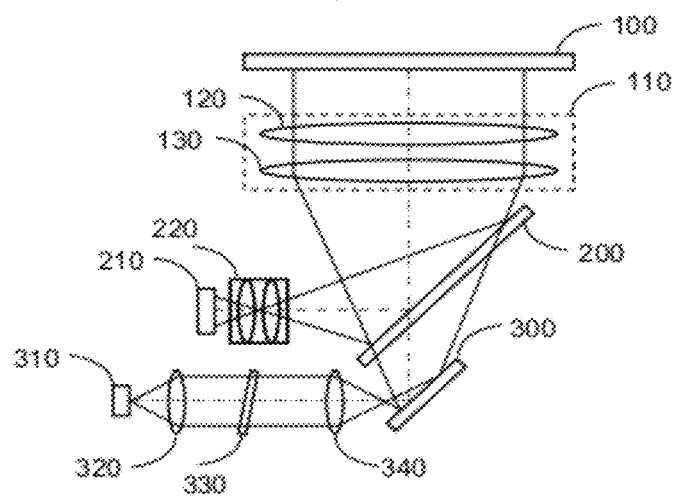
Figure 4:
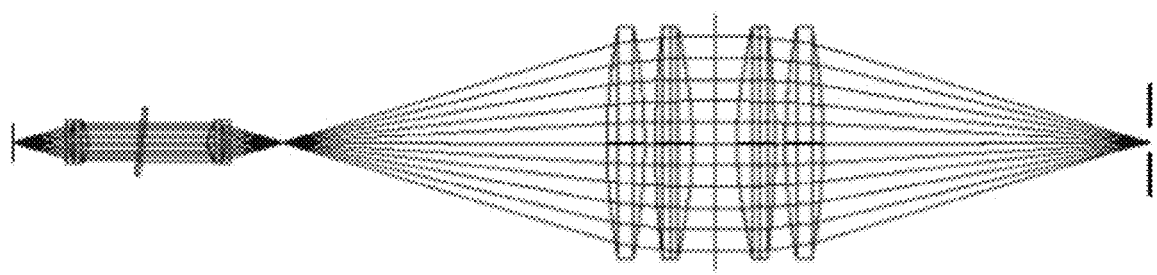
FIG. 4 shows an unfolded optical layout based on an aspheric dual lens objective lens design for full plate imaging.

Referring to the Figures, FIG. 1 is a modified implementation of the scheme shown in FIG. 4 of U.S. Pat. No. 7,599,055. In present FIG. 1 the imaging path and the illumination path share a WFT objective lens optics 110. The sensor microplate 100 is preferably interrogated at a normal incidence angle across the entire area. The uniformity of the incident angle across the full plate can be determined by the aberration of the WFT objective lens 110. Rigorous Coupled Wave Analysis (RCWA) RCWA simulation of the sensor resonance wavelength as a function of incident angle is plotted in FIG. 2. The benefits of normal incidence are three-fold: 1) normal incidence improves the spatial resolution of the sensor (see U.S. Ser. No. 13/021,945, entitled "High resolution label free imaging," first filed Feb. 22, 2010); 2) normal incidence renders the sensor resonance wavelength least sensitive to the angle variation; and 3) normal incidence represents superior conditions of the optics for both illumination and imaging.

The lens group 110 serves as a collimating lens for illumination path and as an objective lens for the imaging path. The focal length of the objective strongly affects the overall size of the instrument. In practice, a lens with F stop (relative aperture) of about 1.4 or less is considered high performance. To cover an entire plate with F/1.4, the focal length is 177 mm. With such a short focal length it is still feasible to design a whole plate reader with a portable footprint.

For collimating the illumination beam, spherical aberration of the lens 110 must be corrected, so that local interrogation angles across the microplate are consistently at normal angle. For the imaging system, it is desirable for the objective lens 110 to minimize the image distortion and aberration. The imaging lens 220 can be, for example, a commercially available CCD or like lens. Its focal length can be estimated by eq. (1):

$$f = d_{CCD} \cdot F_{obj} \qquad (1)$$

where $d_{CCD}$ the width of the CCD or CMOS image sensor, and $F_{obj}$ the F number of the objective lens. Assuming the F number of the CCD lens is equal to that of the objective lens, the entrance aperture stop diameter is about the diagonal distance of the effective image sensor area. The aperture stop diameter must accommodate several aspects or components: 1) the double pass spherical aberration of the objective lens; 2) the necessary tolerance of the local angle variation of the microplate; 3) the size of the extended light source; and 4) the spatial resolution of the imaging system. To tolerate an angle variation of ±5 mrad in a full plate reader, for example, the aperture stop diameter must be larger than 3.5 mm even if the aberration is completely corrected.

EXAMPLES

The following examples serve to more fully describe the manner of using the above-described disclosure, as well as to further set forth the best modes contemplated for carrying out various aspects of the disclosure. It is understood that these examples do not limit the scope of this disclosure, but rather are presented for illustrative purposes. The working examples further describe how to make and use the apparatus and methods of the disclosure.

Example 1

Optical System with Dual Bi-Convex Objective Lens (i.e., a System Most Advantageous for Image Distortion but not Incident Angle)

Figure 2:
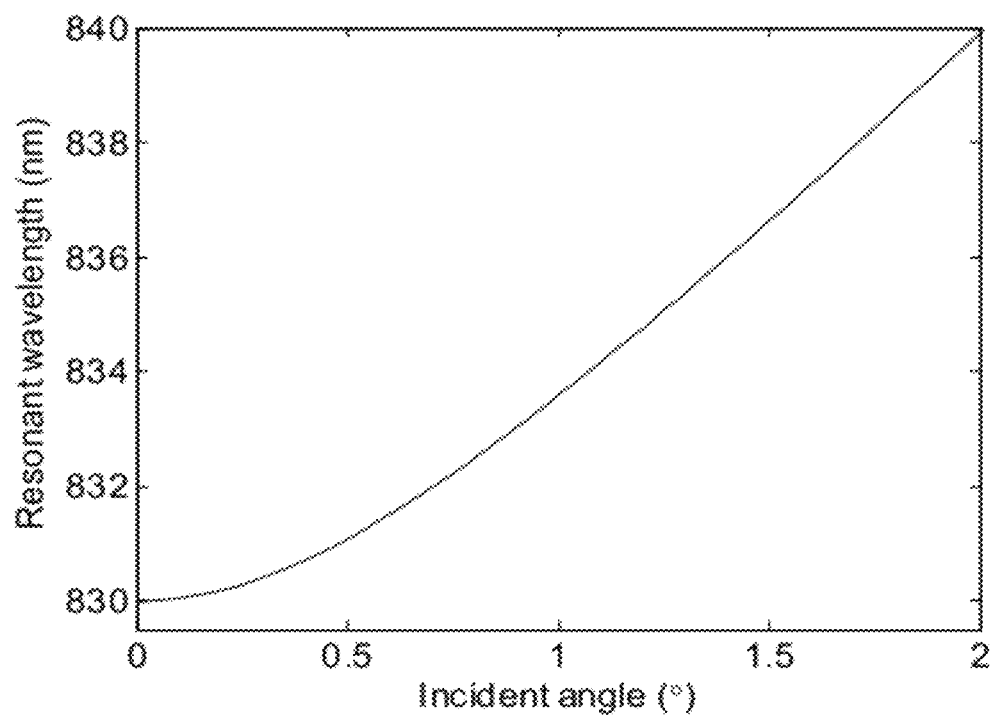
Figure 3:
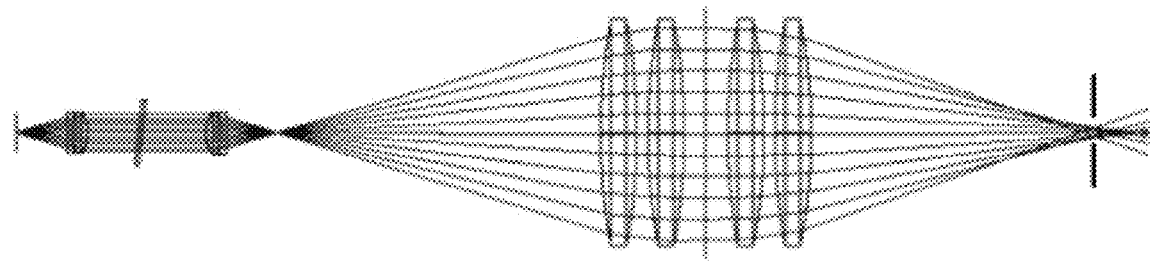
FIG. 3 shows an unfolded optical layout based on a dual bi-convex spherical objective lens design for full plate imaging.
Figure 5A:
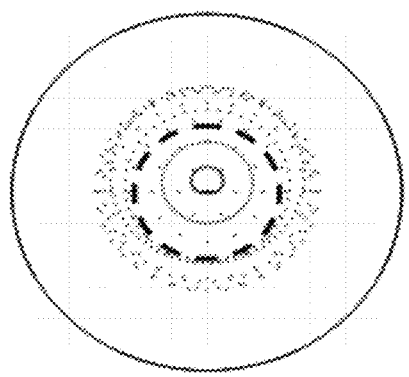
FIGS. 5A and 5B show spot diagrams at the aperture stop plane of the imaging lens as compared to the iris size of a 16 mm F1.4 lens (solid line) and a 6 mm F1.4 lens (dashed line) for a dual bi-convex lens design (5A); and an aspheric lens design (5B).

Spherical aberration of the objective lens can be the most significant contributor to the aperture stop size condition. A singlet lens at F1.4 clearly is unable perform well. We first consider a lens group with two identical biconvex lenses. This design is cost effective. Spherical aberration of this lens group is improved compared to a singlet spherical lens, the minimum spot diameter obtained by ray tracing simulation is about 6 mm, as indicated in FIG. 3 and FIG. 5(a). The iris is positioned at about 26 mm in front of the paraxial focal point because of the spherical aberration. The spot diameter of the rays alone is already larger than the size of a ⅓" image sensor. Appropriate size of the image sensor for this system is larger than ⅔". Image distortion is reduced to 0.44%, as indicated in FIG. 7(a). Spherical aberration renders the ray angles at the object plane substantially different from normal incidence for wells in the outer perimeter. Maximum angle at the edges is 24 mrad, which corresponds to an effective grating tilt angle of 13 mrad, or 0.76°. This angle is large enough to cause a significant resonant wavelength shift of 2.2 nm, as indicated by FIG. 2.

In this embodiment, the biconvex lenses were made by BK7 glass with a radius of curvature of 391 mm. The CMOS image sensor has a 1400×1024 pixels and each pixel measures 7.4 μm×7.4 μm, corresponding to a diagonal distance of 12.8 mm.

Imaging performance of the system is simulated assuming a perfect CCD lens, as illustrated in FIG. 6. Imaging resolution is sufficient for the spatial resolution required for the 1.4 megapixel camera. Distortion is minimized, as indicated in FIG. 7(a).

The design has been implemented in a compact prototype system, the size measuring 10"×4"×10.5". The tunable light source can be, for example, an 830 nm LED 310 (Vishay Semiconductor), a 35 mm focal length collimation lens 320, and an angle tuned filter 330. The narrow band filter has a normal incident center wavelength of 840 nm, and bandwidth of 1 nm. The collimated and filtered light source can be focused by another 35 mm focal length lens 340. The divergent beam is enlarged and collimated by the objective lens group 110.

The CCD lens 220 is a 16 mm megapixel lens from Kowa. The F1.4 lens has a maximum aperture size of 11.4 mm. The minimum beam waist from the illumination beam is positioned at the iris of the CCD lens. Alternatively, the position of the lens relative to the objective lens can fine tune the optical magnification at the expense of smaller tolerance to the plate tilt angle.

FIG. 8 shows a resonant wavelength image of a sensor microplate measured using the edge effects system having a dual bi-convex objective lens. The resonance wavelength of a water filled sensor plate is mapped in FIG. 8, where the corner wells exhibits about 2 nm higher resonance wavelength than those in the center areas due to the increased incident angle as predicted by ray tracing simulation.

FIG. 9 shows a resonant wavelength image of a sensor microplate measured using the system having an aspheric objective lens in Example 4 below.

Illumination uniformity is indicated in FIG. 10. The system has been used for cell assays as well as biochemical assays. The assays results which are based on the shift of resonance is unaffected by the basal resonance wavelength variation.

Example 2

Optical System with Aspheric Objective Lens

Aspheric lens design is developed to further improve the performance. The goal is to generate parallel optical beams to within 1 mrad across the full plate. According to the simulation in FIG. 2, instrument induced wavelength variation can be reduced from about 2 nm to virtually zero. The sensor responses to external perturbations will be consistent across the plate.

A simple method of generating parallel beam at the plane of the microplate is to asperize the focusing lens 340. However, for large spherical aberration, the illumination uniformity is strongly modified. This method also has limited capability to compensate for spherical aberration. Nonetheless, this method can be used to improve the illumination uniformity.

Another equally effective or superior method is to asperize the objective lens. To compare the results using the same prototype design, one of the bi-convex lenses is replaced by an aspheric lens. The preferred aspheric surface can have, for example, a radius of curvature (ROC) of 243 mm, and a conic constant of −9.8. ROC of the second surface can be selected so as to provide very low image distortion. In this instance it has a ROC of 628 mm.

Figure 5B:
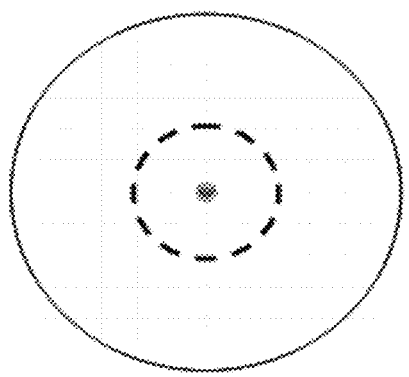

Optical layout of the system is illustrated in FIG. 4. The minimum spot diameter obtained by ray tracing simulation is about 0.6 mm, as indicated in FIG. 5(b). Maximum ray angle is 0.87 mrad, the effective angle is 0.48 mrad, or 0.03°, exceeding the design goal of 1 mrad maximum ray angle error.

A prototype system was demonstrated using the aspheric lens, with the remaining components being identical to the prototype described in Example 1. The F-stop of the imaging lens is placed at the minimum spot position. The F-stop can be closed to F16 without significant vignette, confirming the effective removal of spherical aberration.

The same microplate is mapped in resonance wavelength and resonance reflection power, as shown in FIG. 9 and FIG. 11, respectively. The resonance wavelength exhibits significantly improved uniformity across the plate. The artificially increased wavelength in the corner wells is eliminated. Illumination uniformity across the plate is also substantially improved compared to the previous design.

Example 3

Optical System with Single Element Aspheric Optics

In the two embodiments above, effective focal length of the objective is 200 mm, and the resulting height of the instrument is 267 mm. It is still desirable to further reduce the instrument height. Also note that using aspheric design, a single element objective is feasible.

The following is an example illustrating the optical system design method for a highly compact reader with a single element objective lens while providing uncompromised optical performance.

The focal length of the objective is designed to fit into an instrument enclosure with 200 mm height. The optical layout is illustrated in FIG. 12. A 25 mm focal length plastic aspheric lens is used as the focusing lens 340. The numerical aperture is well matched to the shorter focal length objective. By aspherizing both surfaces of the objective lens, a single element design is feasible. The minimum spot size is comparable to the design in Example 2. Effective focal length of the objective lens is 140 mm, which corresponds to an F number of 1.1.

A 12 mm focal length megapixel CCD lens (Kowa) is used. The imaging performance as illustrated in FIG. 13b suggests comparable performance compared to Example 2. In this instance the lens is deliberately designed to produce a +1.5% pin cushion distortion to compensate for the known −1.5% barrel distortion of the Kowa lens, where % refers to the relative distortion.

The objective lens has a center thickness of 32 mm. The first surface has a radius of curvature (ROC)=105 mm, and a conic=−1.8. The second surface has a ROC=175 mm, and a conic=−4. A bi-aspheric lens can be slightly more costly than using spherical optics in low volume. When using a molding process for volume manufacturing, the lens can still be cost effective.

It is straightforward to apply the design for CCD/CMOS image sensors with difference sizes, and biosensor areas that are half, a quarter, etc., of a microplate. Note that the optical design with the associated tunable light source is applicable to any active imaging system requiring substantially normal incidence angle. The sensors can be interrogated using, for example, swept wavelength imaging, imaging at a few wavelengths, or imaging at a single wavelength.

Example 4

Optical System with Dual Plano-Convex Lenses

Example 1 was further modified for achieving low image distortion. It can be desirable when on-board instrument pipetting is used that the microplate remains within the reader throughout the assay. For applications where on board pipetting is not available, the microplate may need to be removed from the instrument to a separate liquid handling station. Repositioning sensitivity of the microplate can be significant. This is enabled by Examples 2 and 3 above, where the instrument is insensitive to incident angle variation. However, because of the significant manufacturing cost associated with large aperture aspheric lenses, it is desirable to replace the aspheric optics with spherical optics. In this embodiment, the system components are selected for maximizing angular repositioning performance. Although image distortion is not minimized, it can be partially compensated for by the camera lens and further corrected by software.

We first describe a spherical lens design that has the same focal length as Example 1, thereby resulting in a comparable instrument footprint. The system is designed to provide minimum incidence angle over the full micro plate. We consider a two element spherical objective lens design for cost effectiveness. Additional or alternative elements can be include and refined in a similar manner. The system is depicted in FIG. 14, where the lens prescriptions are: ROC1=246 mm; ROC2=−1701 mm; ROC3=129 mm; ROC4=310 mm, and the material is Bk7 glass. The interrogation angle can be, for example, preferably less than 1 mrad across the microplate. Such a performance is very close to that of the aspheric lens. Minimum beam size can be, for example, 1.2 mm, which also enables the used of low cost ⅓" imager sensors, as indicated in FIG. 15. Image distortion can be, for example, 4.5%.

To further reduce the manufacturing cost, a simplified design using two identical plano-convex lenses was explored. The system is illustrated in FIG. 17. The radius of curvature of the convex surface can be, for example, 213 mm. The interrogation angle can be, for example, preferably less than 2 mrad across the micro plate. Minimum spot size of the stop of the imaging lens can be 2.4 mm, which also enables the used of low cost ⅓" imager sensors, as indicated in FIG. 18. The margin can accommodate micro plate tile angle of ±2.8 mrad without vignette. This margin can be further increased by using camera lenses with lower F numbers. For instance, a 1.0 F number can accommodate microplate tile angle of ±5 mrad, which potentially can relax the manufacturing requirements of micro plates. Image distortion is improved to 3%. This can be partially compensated by the typical negative distortion of the camera lens. Image distortion in generate and be corrected by software.

According to the simulation of FIG. 2, an incident angle less than 2 mrad is sufficient for low angle sensitivity. A 2 mrad value is also comparable to the typical plate flatness.

The system performance can be further improved, for example, by increasing the effective focal length of the objective lens. For example, increasing the effective focal length by 50 mm can also bring down the incidence angle to less than 1 mrad with a dual plano-convex lens design.

The disclosure has been described with reference to various specific embodiments and techniques. However, it should be understood that many variations and modifications are possible while remaining within the scope of the disclosure.

What is claimed is:

1. A compact microplate imaging system, comprising:
   a tunable spatially incoherent light source having a spectral width substantially similar to the resonance width of at least one sensor of a user provided microplate;
   a lens ensemble having a focusing lens and an objective lens to collimate the tunable spatially incoherent light from the source onto the user provided microplate and to transmit light that is reflected from the microplate to an image sensor;
   a beam splitter to divert a portion of the reflected light to the image sensor; and an imaging lens to collect diverted light and to produce an optical image of the at least one sensor of the microplate;

wherein the image sensor receives the optical image of the at least one sensor of the microplate, and the collimated tunable incoherent light is directed to the user provided microplate at normal incidence.

2. The system of claim 1 wherein the co-action of the focusing lens and the objective lens comprise a beam expander.

3. The system of claim 1 wherein the objective lens comprises a lens group comprising two spherical lenses.

4. The system of claim 1 wherein the objective lens comprises a single aspheric surface.

5. The system of claim 1 wherein the objective lens comprises at least two aspheric surfaces.

6. The system of claim 1 wherein the tunable spatially incoherent light source comprises a substantially collimated LED and a tunable optical filter.

7. The system of claim 1 wherein the reflected beam from the at least one sensor of the microplate passes through the same beam splitter, the imaging lens, and at least the objective lens of the lens ensemble, prior to forming an image on the image sensor.

8. The system of claim 1 wherein the image sensor comprises a CCD, a CMOS, or a combination thereof.

9. The system of claim 1 wherein an optical stop of the imaging lens is positioned at the focal point of the objective lens.

10. The system of claim 1 wherein the objective lens is an aspheric lens and provides uniform illumination on a microplate.

11. The system of claim 1 wherein the distortion of the objective lens compensates for the distortion from the imaging lens.

12. The system of claim 1 wherein the microplate comprises two or more microplates.

13. The system of claim 1 wherein the microplate comprises a fractional portion of a microplate.

14. The system of claim 1 wherein the imaging system has a footprint of about 40 square inches and a volume of about 320 to 440 cubic inches.

15. A method for interrogating a resonance waveguide sensor of a microplate with the system of claim 1 comprising:

emitting an optical beam from the tunable spatially incoherent source light source having a spectral width substantially similar to the resonance width of at least one sensor of the user provided microplate;

converting the optical beam into one or more interrogation beams with the lens ensemble;

illuminating one or more sensors of the microplate with the one or more of the interrogation beams at normal incidence;

collecting the reflected light of the illuminated one or more sensors; and forming an image on the image sensor.

16. The method of claim 15 wherein the microplate comprises a multiplicity of microplates, a single microplate, a fractional portion of a microplate, or a combination thereof.

17. An apparatus for label free imaging comprising:
an optical reader comprising:
a receptacle to receive a user provided microplate having at least one optical sensor;
a tunable spatially incoherent light source having a spectral width substantially similar to the resonance width of at least one sensor of the user provided microplate;
a lens ensemble having an imaging lens, a focusing lens, and an objective lens, which ensemble collimates the tunable spatially incoherent light source on the microplate at normal incidence and transmits light reflected from the microplate at normal incidence;
a beam splitter which diverts a portion of the transmitted light;
and
an image sensor which receives a portion of the transmitted light and images the transmitted light.

18. A method of reading an evanescent wave sensor in the apparatus of claim 17, comprising:
forming a microplate assembly by engaging the receptacle with a microplate having a well, and at least one well having at least one sensor;
illuminating the microplate with the collimated tunable spatially incoherent light source;
collecting the reflected light from the illuminated microplate; and
forming an image of the reflected light on the image sensor.

* * * * *